US00PP08105P

United States Patent [19]

VandenBerg

[11] Patent Number: Plant 8,105

[45] Date of Patent: Jan. 19, 1993

[54] CHRYSANTHEMUM PLANT NAMED CONGA

[75] Inventor: Cornelis P. VandenBerg, Salinas, Calif.

[73] Assignee: Yoder Brothers, Inc., Barberton, Ohio

[21] Appl. No.: 715,633

[22] Filed: Jun. 14, 1991

[51] Int. Cl.[5] ..... A01H 5/00

[52] U.S. Cl. ..... Plt./74.1

[58] Field of Search ..... Plt./74, 74.1

[56] References Cited

U.S. PATENT DOCUMENTS

P.P. 3,945 8/1976 Jessel, Jr. et al. ..... Plt. 74

P.P. 6,143 4/1988 van der Jagt ..... Plt. 74

*Primary Examiner*—Howard J. Locker

*Attorney, Agent, or Firm*—Foley & Lardner

[57] ABSTRACT

A Chrysanthemum plant named Conga particularly characterized by its flat capitulum form; daisy capitulum type; dark red-purple ray floret color; diameter across face of capitulum of 64 to 79 mm when fully opened, when grown as a single stem spray cut mum; flowering response in Salinas under normal temperatures is 50 to 53 days after start of short days, and flowering response in Bogota, Colombia under temperatures of minimum 6.3 degrees Celsius night and maximum 29 degrees Celsius day is 63 to 68 days; plant height is 79 to 91 cm when grown in Salinas with 6 to 14 long days prior to start of short days compared to a height of 91 to 102 cm when grown in Botoga with 14 to 17 long days prior to start of short days; peduncle length of the first lateral at flowering after removing the apical bud without growth regulator applications is 8 to 13 cm when grown both in Salinas and in Bogota and peduncle length of the fourth lateral at flowering is 10 to 15 cm when grown in Salinas, and 13 to 18 cm when grown in Bogota; and excellent tolerance to low night temperatures for bud initiation and flower development.

3 Drawing Sheets

1

The present invention comprises a new and distinct cultivar of Chrysanthemum, botanically known as *Dendranthema grandiflora,* and referred to by the cultivar name Conga.

Conga, identified as 1873 (87-434003), was originated from a cross made by Cornelis P. VandenBerg in a controlled breeding program in Salinas, Calif., in August 1986.

The female parent of Conga was an unnamed seedling, identified as 6826 (84-187015), and described as a dark pink daisy cut spray mum having a flowering response to short days of 53 to 67 days when grown in Salinas, Calif., and 70 to 74 days when grown in Bogota, Colombia; and a plant height of 64 to 99 cm when grown with 7 to 15 long days prior to start of short days in Salinas, Calif., and 107 to 117 cm with 14 long days prior to start of short days when grown in Bogota, Colombia. The diameter of capitulum of the female parent was not recorded in our Salinas and Bogota flowering trials. The female parent was discarded from the Salinas flowering trials in July 1987, and was discarded from the Bogota trials in October 1987.

The male parent of Conga was an unnamed seedling, identified as 5971 (82-J20070), and described as an orange-bronze daisy spray cut mum having a flowering response to short days of 53 to 64 days in Salinas, Calif., and 70 days in Bogota, Colombia; and a plant height of 66 to 99 cm with 11 to 14 long days prior to start of short days when grown in Salinas, Calif., and 94 to 109 cm when grown with 14 long days prior to start of short days in Bogota, Colombia. The diameter of capitulum of the male parent of Conga was 70 to 76 mm. The male parent was discarded from the Bogota flowering programs in April 1986, and was discarded from all programs after completion of the seed production program that eventually led to discovering and selection of the cultivar Conga.

2

Conga was discovered and selected as one flowering plant within the progeny of the stated cross by Cornelis P. VandenBerg in November 1987, in a controlled environment in Salinas, Calif.

The first act of asexual reproduction of Conga was accomplished when vegetative cuttings were taken from the initial selection in January 1988 in a controlled environment in Salinas, Calif., by technicians working under supervision of Cornelis P. VandenBerg.

Horticultural examination of controlled flowerings of successive plantings has shown that the unique combination of characteristics as herein disclosed for Conga are firmly fixed and are retained through successive generations of asexual reproduction.

Conga has not been observed under all possible environmental conditions. The phenotype may vary significantly with variations in environment such as temperature, light intensity and daylength.

The following observations, measurements and comparisons describe plants grown in Salinas, Calif., and in Bogota, Colombia, under greenhouse conditions which approximate those generally used in commercial greenhouse practice. The low temperature tolerance was determined in repeated flowerings in Bogota, Colombia, with an average minimum low night temperature inside thegreenhouse during our trials ranging from 6.3 to 10.0 degrees Celsius.

The following traits have been repeatedly observed and are determined to be basic characteristics of Conga, which, in combination, distinguish this Chrysanthemum as a new and distinct cultivar:

1. Flat capitulum form.
2. Daisy capitulum type.
3. Dark red-purple ray floret color.

4. Diameter across face of capitulum of 64 to 79 mm when fully opened, when grown as a single stem spray cut mum.
5. Flowering response in Salinas under normal temperatures is 50 to 53 days after start of short days. Flowering response in Bogota, Colombia under temperatures of minimum 6.3 degrees Celsius night and maximum 29 degrees Celsius day is 63 to 68 days.
6. Plant height is 79 to 91 cm when grown in Salinas with 6 to 14 long days prior to start of short days; height is 91 to 102 cm when grown in Bogota with 14 to 17 long days prior to start of short days.
7. Peduncle length of the first lateral at flowering after removing the apical bud without growth regulator applications is 8 to 13 cm when grown both in Salinas and in Bogota. Peduncle length of the fourth lateral at flowering is 10 to 15 cm when grown in Salinas, and 13 to 18 cm when grown in Bogota.
8. Excellent tolerance to low night temperatures for bud initiation and flower development.

The accompanying photographic drawings show typical inflorescence and leaf characteristics of Conga, with the colors being as nearly true as possible with illustrations of this type.

Sheet 1 is a color photograph of Conga grown as a single stem spray cut mum in Salinas, Calif.

Sheet 2 is a black and white photograph of three views of the inflorescence of Conga.

Sheet 3 is a black and white photograph showing the upper and under sides of the leaves of Conga at 3 stages of development (mature, intermediate and immature). In sheet 2 a measuring tape in centimeters has been added.

Of the commercial cultivars known to the inventor, the most similar in comparison to Conga is the cultivar identified as Accent, disclosed in U.S. Plant Pat. No. 3,945. Reference is made to attached Chart A, which compares certain characteristics of Conga to the same characteristics of Accent.

Similar traits are ray floret color, capitulum form and type, flowering response to short days when grown in Salinas, Calif., and spray formation. Conga has a smaller diameter of capitulum when compared with Accent, and more vigor. Also, Accent has a very poor low night temperature tolerance and cannot be grown commercially under normal environmental conditions of Bogota, Colombia, while Conga has excellent tolerance to the Bogota low night temperatures.

When compared with both parents, Conga has a faster flowering response when grown both in Salinas and in Bogota than either parent. In addition, both parents were discarded from all programs because of overall unsatisfactory performance worldwide, while the overall performance of Conga in the United States and Colombia warrants commercial introduction.

In the following description color references are made to The Royal Horticultural Society Colour Chart. The color values were determined on plant material grown as a single stem spray cut mum in Salinas, Calif. on Sep. 12, 1990.

Classification:

*Botanical.*—*Dendranthema grandiflora* cv Conga.

*Commercial.*—Daisy spray cut mum.

INFLORESCENCE

A. Capitulum:

*Form.*—Flat.

*Type.*—Daisy.

*Diameter across face.*—64 to 79 mm when fully opened.

B. Corolla of ray florets:

*Color (general tonality from a distance of three meters).*—Dark red-purple.

*Color (upper surface).*—71B.

*Color (under surface).*—75B to 75C.

*Shape.*—Flat, straight. Some ray florets are slightly indented; young, opening flowers show longitudinal petal roll. See photograph.

C. Corolla of disc florets:

*Color (mature).*—14A.

*Color (immature).*—14A, strongly overlaid with 144B.

D. Reproductive organs:

*Androecium.*—Present on disc florets only; no pollen.

*Gynoecium.*—Present on both ray and disc florets.

PLANT

A. General appearance:

*Height.*—79 to 91 cm when grown in Salinas with 6 to 14 long days prior to start of short days, and 91 to 102 cm when grown in Bogota with 14 to 17 long days prior to start of short days.

B. Foliage:

*Color (upper surface).*—147A.

*Color (under surface).*—147B.

*Shape.*—See photograph.

CHART A

COMPARISON OF CONGA AND ACCENT

| CHARACTERISTIC | CONGA | ACCENT |
|---|---|---|
| Ray floret color | Dark red-purple | Dark red-purple |
| Capitulum form and type | Flat daisy | Flat daisy |
| Diameter across face of capitulum | 64 to 79 mm | 70 to 91 mm |
| Flowering response: | | |
| in Salinas | 50 to 53 days | 50 to 57 days |
| in Bogota | 63 to 68 days | not available |
| Plant height: | | |
| 6–14 long days Salinas | 99 to 119 cm | |
| 14 long days Salinas | | 58 to 102 cm |
| Peduncle length: | | |
| 1st lateral Salinas | 8 to 13 cm | 3 to 10 cm |
| 4th lateral Salinas | 10 to 15 cm | 13 to 20 cm |
| Spray formation | Terminal | Terminal |
| Low night temperature tolerance | Excellent | Poor |

COMPARISONS MADE OF PLANTS GROWN AS SINGLE STEM SPRAY CUT MUMS IN SALINAS, CALIFORNIA

I claim:

1. A new and distinct Chrysanthemum plant named Conga, as described and illustrated.

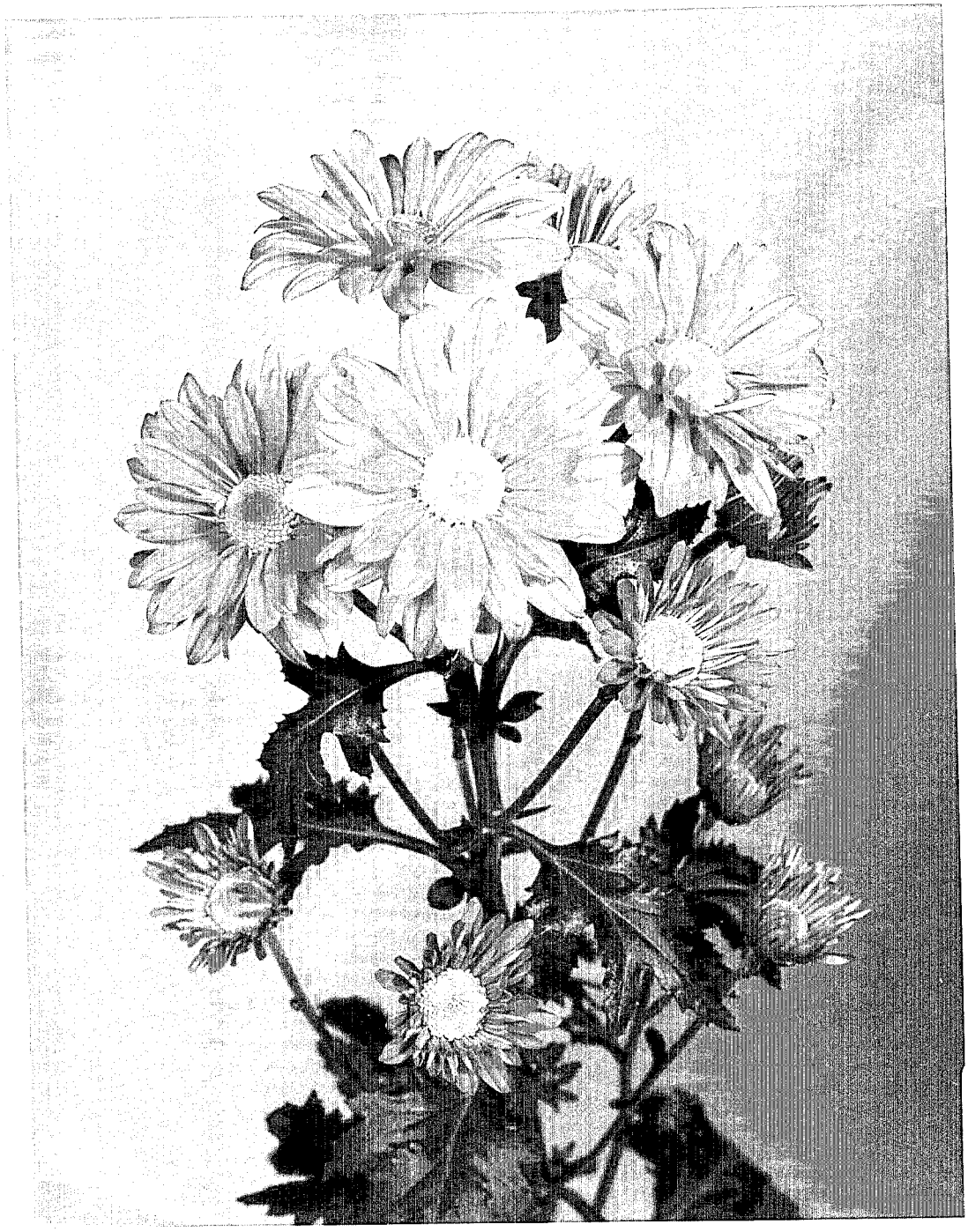

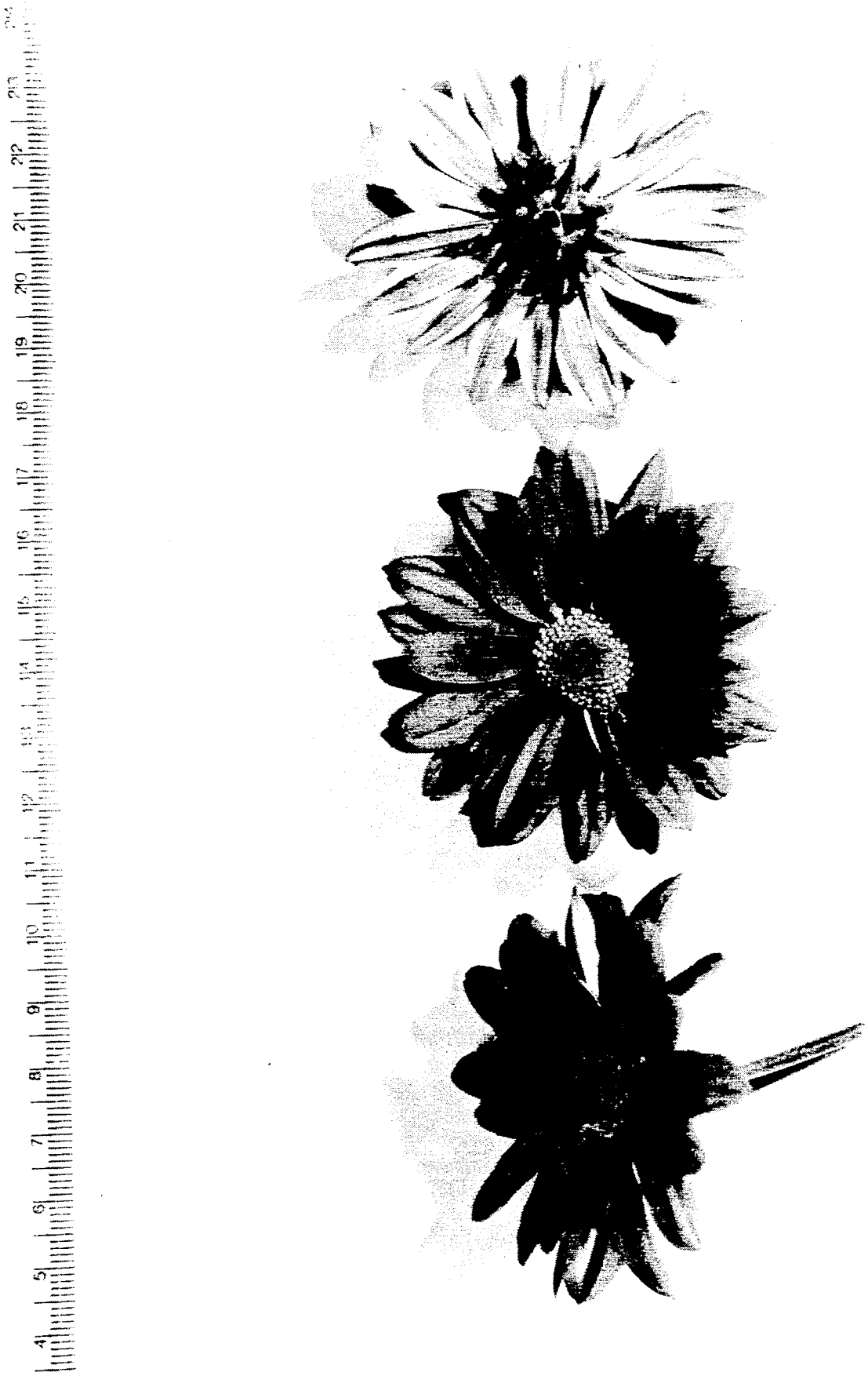

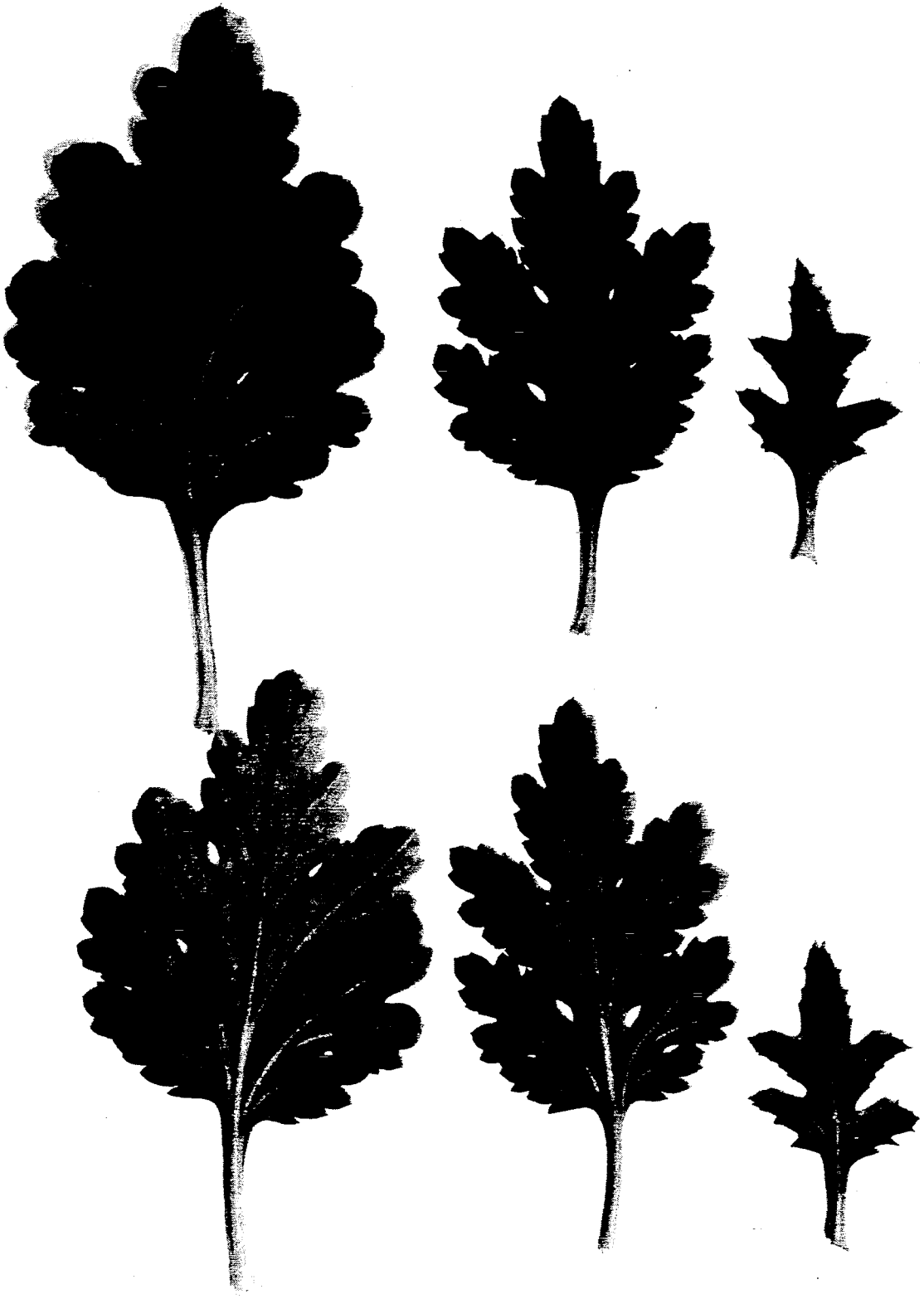

* * * * *